United States Patent
Honda et al.

(10) Patent No.: US 12,213,722 B2
(45) Date of Patent: Feb. 4, 2025

(54) APPARATUS AND METHOD FOR ELECTROSURGERY

(71) Applicant: OLYMPUS MEDICAL SYSTEMS CORP., Tokyo (JP)

(72) Inventors: Satoshi Honda, Hachioji (JP); Shunsuke Matsui, Hachioji (JP); Danilo Legaspi, Hachioji (JP); Akinori Kabaya, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 665 days.

(21) Appl. No.: 17/546,374

(22) Filed: Dec. 9, 2021

(65) Prior Publication Data
US 2022/0265338 A1    Aug. 25, 2022

Related U.S. Application Data

(60) Provisional application No. 63/151,993, filed on Feb. 22, 2021.

(51) Int. Cl.
*A61B 18/12* (2006.01)
*A61B 18/00* (2006.01)

(52) U.S. Cl.
CPC .. *A61B 18/1206* (2013.01); *A61B 2018/0063* (2013.01); *A61B 2018/00755* (2013.01)

(58) Field of Classification Search
CPC .............. A61B 18/085; A61B 18/1206; A61B 2018/0063; A61B 2018/00702; A61B 2018/00755; A61B 2018/00875; A61B 2018/00916
See application file for complete search history.

(56) References Cited

U.S. PATENT DOCUMENTS

| | | | |
|---|---|---|---|
| 7,972,328 B2 | 7/2011 | Wham et al. | |
| 2003/0105411 A1* | 6/2003 | Smallwood | A61B 5/053 600/547 |
| 2008/0039831 A1* | 2/2008 | Odom | A61B 18/1445 606/51 |
| 2018/0333185 A1* | 11/2018 | Asher | A61B 18/1442 |

\* cited by examiner

*Primary Examiner* — Tigist S Demie
(74) *Attorney, Agent, or Firm* — Morgan, Lewis & Bockius LLP

(57) ABSTRACT

Methods and systems for sealing biological tissue using high frequency electrical energy determines a first-instance size of the biological tissue based on an initial impedance determination and applies electrical energy to the biological tissue based on the first-instance size determination, during which an in-process parameter is detected. A second-instance size of the biological tissue is determined based on the detected in-process parameter. When the second-instance size is different from the first-instance size, the second-instance electrical energy is different than the first-instance electrical energy; and when the second-instance size is the same as the first-instance size, the second-instance electrical is the same as the first-instance electrical energy. In-process parameter include (i) a value of in-process impedance of the biological tissue, (ii) a rate of change of the in-process impedance of the biological tissue, (iii) a value of in-process integrated power delivered to the biological tissue, or (iv) a combination thereof.

20 Claims, 7 Drawing Sheets

APPARATUS AND METHOD FOR ELECTROSURGERY

RELATED APPLICATION DATA

This application is based on and claims priority under 35 U.S.C. § 119 to U.S. Provisional Application No. 63/151,993, filed on Feb. 22, 2021, the entire contents of which is incorporated herein by reference.

TECHNICAL FIELD

The systems, devices and methods disclosed herein are directed to electrosurgery and in particular to electrothermal tissue sealing.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Many medical procedures include sealing a biological tissue, such as a blood vessel. One of the techniques used for sealing blood vessels is called electrothermal sealing. During an electrothermal sealing procedure, a high frequency electric current is applied to the biological tissue to be sealed, such as a blood vessel of a patient. The current results in localized heating of the biological tissue causing the tissue to dehydrate and proteins like collagen and elastin in the tissue to denature, which forms the seal.

The amount of electrical energy and the amount of time for which the electrical energy is provided during the sealing procedure typically depends on the size of the biological tissue. Conventionally, such determination of tissue size is made based on an initial impedance value determined for the biological tissue that is acquired by constant power control applied at the initiation of the sealing procedure. This initial impedance value is then used in the procedure as a basis for the amount of output voltage (in the first instance) that is applied to the tissue during sealing.

Having an inaccurate size determination can lead to applying too high an output voltage to the tissue and/or applying an output voltage to the tissue for too long a time period (relative to what is appropriate for the tissue size), which can result in longer procedures than necessary, result in poor quality seals, and/or lead to tissue damage that may have otherwise been avoidable. Thus, there is a need for improved techniques to accurately determine the size of the biological tissue for use in the sealing procedure, and thereby improve the sealing time and quality of the sealing, for example, by reducing the sealing time and applying the appropriate output voltage while minimizing the damage to the biological tissue.

SUMMARY

To address the above-noted issues in electrothermal sealing, improved techniques are needed to accurately determine the size of the biological tissue for use in the sealing procedure, and thereby improve the sealing procedure and quality of the sealing, for example, by reducing the sealing time and applying the appropriate output voltage while minimizing the damage to the biological tissue. The present inventors observed that by measuring certain parameters during the electrothermal sealing procedure, such as (i) a rate of change in the value of tissue impedance, (ii) a value of tissue impedance above a certain threshold value, (iii) a value of integrated power below a certain threshold value, or combinations of such certain parameters (each of which can be correlated to tissue size), the size of the tissue can be more accurately determined. Additionally, one can use information on such parameters to re-determine the size of the tissue and to change, update or otherwise modulate the parameters associated with the electrothermal sealing procedure, e.g., dynamically during the electrothermal sealing procedure itself. Advantageously, such a dynamic procedure improves the efficiency and speed of sealing the tissue, the quality of the sealing, and minimizes the damage to the biological tissue.

Accordingly, a method for sealing a tissue using high frequency electrical energy includes In one aspect of the present disclosure, a method for sealing a biological tissue using high frequency electrical energy comprises determining a first-instance size of the biological tissue based on an initial impedance determination and applying electrical energy to the biological tissue based on the first-instance size determination, during which an in-process parameter is detected. A second-instance size of the biological tissue is determined based on the detected in-process parameter. When the second-instance size is different from the first-instance size, the second-instance electrical energy is different than the first-instance electrical energy; and when the second-instance size is the same as the first-instance size, the second-instance electrical is the same as the first-instance electrical energy. In-process parameter include (i) a value of in-process impedance of the biological tissue, (ii) a rate of change of the in-process impedance of the biological tissue, (iii) a value of in-process integrated power delivered to the biological tissue, or (iv) a combination thereof. A second-instance size of the biological tissue is determined based on the detected in-process parameter. A second-instance electrical energy is applied to the biological tissue. A value of voltage of the second-instance electrical energy and a length of time of application of the second-instance electrical energy are both based on the second-instance size of the biological tissue.

In some embodiments, when the first-instance size of the biological tissue based on the initial impedance is large and the value of in-process impedance of the biological tissue is greater than 200Ω, then the second-instance size of the biological tissue is determined as small. The second-instance electrical energy to the biological tissue is different than the first-instance electrical energy to the biological tissue.

In some embodiments, the value of in-process impedance of the biological tissue is 200Ω to 500Ω.

In some embodiments, the in-process parameter is the rate of change of the in-process impedance of the biological tissue.

In some embodiments, when the first-instance size of the biological tissue based on the initial impedance is large and the rate of change of the in-process impedance of the biological tissue is greater than 1000 Ω/s, then the second-instance size of the biological tissue is determined as small. The second-instance electrical energy to the biological tissue is different than the first-instance electrical energy to the biological tissue.

In some embodiments, the rate of change of the in-process impedance of the biological tissue is 1000 Ω/s to 1500 Ω/s.

In some embodiments, the in-process parameter is the value of in-process integrated power delivered to the biological tissue.

In some embodiments, when the first-instance size of the biological tissue based on the initial impedance is large and the value of in-process integrated power delivered to the biological tissue is less than 15 J, then the second-instance size of the biological tissue is determined as small. The second-instance electrical energy to the biological tissue is different than the first-instance electrical energy to the biological tissue.

In some embodiments, when the second-instance size of the biological tissue is different than the first-instance size of the biological tissue, the second-instance electrical energy to the biological tissue is different than the first-instance electrical energy to the biological tissue.

In some embodiments, when the second-instance size of the biological tissue is the same as the first-instance size of the biological tissue, the second-instance electrical energy to the biological tissue is the same as the first-instance electrical energy to the biological tissue.

In an aspect of the present disclosure, a system for sealing a biological tissue comprises an energy source configured to generate high frequency electrical energy. An end effector is operably connected to the energy source and is configured to provide the high frequency electrical energy to the biological tissue. A controller is operably connected to the energy source. The controller is configured to determine an initial impedance of the biological tissue. A first-instance size of the biological tissue is determined based on an initial impedance determination and electrical energy is applied to the biological tissue based on the first-instance size determination, during which an in-process parameter is detected. A second-instance size of the biological tissue is determined based on the detected in-process parameter. When the second-instance size is different from the first-instance size, the second-instance electrical energy is different than the first-instance electrical energy; and when the second-instance size is the same as the first-instance size, the second-instance electrical is the same as the first-instance electrical energy. In-process parameter include (i) a value of in-process impedance of the biological tissue, (ii) a rate of change of the in-process impedance of the biological tissue, (iii) a value of in-process integrated power delivered to the biological tissue, or (iv) a combination thereof. A second-instance size of the biological tissue is determined based on the detected in-process parameter. A second-instance electrical energy is applied to the biological tissue. A value of voltage of the second-instance electrical energy and a length of time of application of the second-instance electrical energy are both based on the second-instance size of the biological tissue.

In some embodiments, the controller is configured to apply the second-instance electrical energy is to the biological tissue until sealing of the tissue is complete.

In some embodiments, when the second-instance size of the biological tissue is different than the first-instance size of the biological tissue, the second-instance electrical energy to the biological tissue is different than the first-instance electrical energy to the biological tissue.

In some embodiments, when the second-instance size of the biological tissue is the same as the first-instance size of the biological tissue, the second-instance electrical energy to the biological tissue is the same as the first-instance electrical energy to the biological tissue.

In some embodiments, the in-process parameter is the value of in-process impedance of the biological tissue.

In some embodiments, when the first-instance size of the biological tissue based on the initial impedance is large and the value of in-process impedance of the biological tissue is less than 100Ω, then the second-instance size of the biological tissue is determined as large. The second-instance electrical energy to the biological tissue is the same as the first-instance electrical energy to the biological tissue.

In some embodiments, when the first-instance size of the biological tissue based on the initial impedance is small and the value of in-process impedance of the biological tissue is greater than 100Ω, then the second-instance size of the biological tissue is determined as small. The second-instance electrical energy to the biological tissue is the same as the first-instance electrical energy to the biological tissue.

In some embodiments, the value of in-process impedance of the biological tissue is 100Ω to 200Ω.

In some embodiments, when the first-instance size of the biological tissue based on the initial impedance is large and the value of in-process impedance of the biological tissue is greater than 200Ω then the second-instance size of the biological tissue is determined as small. The second-instance electrical energy to the biological tissue is different than the first-instance electrical energy to the biological tissue.

In some embodiments, the value of in-process impedance of the biological tissue is 200Ω to 500Ω.

In some embodiments, the in-process parameter is the rate of change of the in-process impedance of the biological tissue.

In some embodiments, when the first-instance size of the biological tissue based on the initial impedance is large and the rate of change of the in-process impedance of the biological tissue is less than 400 Ω/s, then the second-instance size of the biological tissue is determined as large. The second-instance electrical energy to the biological tissue is the same as the first-instance electrical energy to the biological tissue.

In some embodiments, when the first-instance size of the biological tissue based on the initial impedance is small and the rate of change of the in-process impedance of the biological tissue is greater than 400 Ω/s, then the second-instance size of the biological tissue is determined as small. The second-instance electrical energy to the biological tissue is the same as the first-instance electrical energy to the biological tissue.

In some embodiments, the rate of change of the in-process impedance of the biological tissue is 400 Ω/s to 600 Ω/s.

In some embodiments, when the first-instance size of the biological tissue based on the initial impedance is large and the rate of change of the in-process impedance of the biological tissue is greater than 1000 Ω/s, then the second-instance size of the biological tissue is determined as small. The second-instance electrical energy to the biological tissue is different than the first-instance electrical energy to the biological tissue.

In some embodiments, the rate of change of the in-process impedance of the biological tissue is 1000 Ω/s to 1500 Ω/s.

In some embodiments, the in-process parameter is the value of in-process integrated power delivered to the biological tissue.

In some embodiments, when the first-instance size of the biological tissue based on the initial impedance is large and the value of in-process integrated power delivered to the biological tissue is greater than 20 J, then the second-instance size of the biological tissue is determined as large.

The second-instance electrical energy to the biological tissue is the same as the first-instance electrical energy to the biological tissue.

In some embodiments, the value of in-process integrated power delivered to the biological tissue is 20 J to 50 J.

In some embodiments, when the first-instance size of the biological tissue based on the initial impedance is large and the value of in-process integrated power delivered to the biological tissue is less than 15 J, then the second-instance size of the biological tissue is determined as small. The second-instance electrical energy to the biological tissue is different than the first-instance electrical energy to the biological tissue.

In an aspect of the present disclosure, a controller for a device for sealing a biological tissue is operably connected to an energy source. The controller is configured to determine an initial impedance of the biological tissue. A first-instance size of the biological tissue is determined based on an initial impedance determination and electrical energy is applied to the biological tissue based on the first-instance size determination, during which an in-process parameter is detected. A second-instance size of the biological tissue is determined based on the detected in-process parameter. When the second-instance size is different from the first-instance size, the second-instance electrical energy is different than the first-instance electrical energy; and when the second-instance size is the same as the first-instance size, the second-instance electrical is the same as the first-instance electrical energy. In-process parameter include (i) a value of in-process impedance of the biological tissue, (ii) a rate of change of the in-process impedance of the biological tissue, (iii) a value of in-process integrated power delivered to the biological tissue, or (iv) a combination thereof. A second-instance size of the biological tissue is determined based on the detected in-process parameter. A second-instance electrical energy is applied to the biological tissue. A value of voltage of the second-instance electrical energy and a length of time of application of the second-instance electrical energy are both based on the second-instance size of the biological tissue.

In some embodiments, the controller is configured to apply the second-instance electrical energy is to the biological tissue until sealing of the tissue is complete.

In some embodiments, when the second-instance size of the biological tissue is different than the first-instance size of the biological tissue, the second-instance electrical energy to the biological tissue is different than the first-instance electrical energy to the biological tissue.

In some embodiments, when the second-instance size of the biological tissue is the same as the first-instance size of the biological tissue, the second-instance electrical energy to the biological tissue is the same as the first-instance electrical energy to the biological tissue.

In some embodiments, the in-process parameter is the value of in-process impedance of the biological tissue.

In some embodiments, when the first-instance size of the biological tissue based on the initial impedance is large and the value of in-process impedance of the biological tissue is less than 100Ω, preferably less than 80Ω, then the second-instance size of the biological tissue is determined as large. The second-instance electrical energy to the biological tissue is the same as the first-instance electrical energy to the biological tissue.

In some embodiments, when the first-instance size of the biological tissue based on the initial impedance is small and the value of in-process impedance of the biological tissue is greater than 80Ω, preferably greater than 100Ω, then the second-instance size of the biological tissue is determined as small. The second-instance electrical energy to the biological tissue is the same as the first-instance electrical energy to the biological tissue.

In some embodiments, the value of in-process impedance of the biological tissue is 100Ω to 200Ω.

In some embodiments, when the first-instance size of the biological tissue based on the initial impedance is large and the value of in-process impedance of the biological tissue is greater than 200Ω, then the second-instance size of the biological tissue is determined as small. The second-instance electrical energy to the biological tissue is different than the first-instance electrical energy to the biological tissue.

In some embodiments, the value of in-process impedance of the biological tissue is 200Ω to 500Ω.

In some embodiments, the in-process parameter is the rate of change of the in-process impedance of the biological tissue.

In some embodiments, when the first-instance size of the biological tissue based on the initial impedance is large and the rate of change of the in-process impedance of the biological tissue is less than 400 Ω/s, then the second-instance size of the biological tissue is determined as large. The second-instance electrical energy to the biological tissue is the same as the first-instance electrical energy to the biological tissue.

In some embodiments, when the first-instance size of the biological tissue based on the initial impedance is small and the rate of change of the in-process impedance of the biological tissue is greater than 400 Ω/s, then the second-instance size of the biological tissue is determined as small. The second-instance electrical energy to the biological tissue is the same as the first-instance electrical energy to the biological tissue.

In some embodiments, the rate of change of the in-process impedance of the biological tissue is 400 Ω/s to 600 Ω/s.

In some embodiments, when the first-instance size of the biological tissue based on the initial impedance is large and the rate of change of the in-process impedance of the biological tissue is greater than 1000 Ω/s, then the second-instance size of the biological tissue is determined as small. The second-instance electrical energy to the biological tissue is different than the first-instance electrical energy to the biological tissue.

In some embodiments, the rate of change of the in-process impedance of the biological tissue is 1000 Ω/s to 1500 Ω/s.

In some embodiments, the in-process parameter is the value of in-process integrated power delivered to the biological tissue.

In some embodiments, when the first-instance size of the biological tissue based on the initial impedance is large and the value of in-process integrated power delivered to the biological tissue is greater than 20 J, then the second-instance size of the biological tissue is determined as large. The second-instance electrical energy to the biological tissue is the same as the first-instance electrical energy to the biological tissue.

In some embodiments, the value of in-process integrated power delivered to the biological tissue is 20 J to 50 J.

In some embodiments, when the first-instance size of the biological tissue based on the initial impedance is large and the value of in-process integrated power delivered to the biological tissue is less than 15 J, then the second-instance size of the biological tissue is determined as small. The second-instance electrical energy to the biological tissue is different than the first-instance electrical energy to the biological tissue.

Additional features and advantages will be set forth in the description that follows, and in part will be apparent from the description, or may be learned by practice of the invention. The objectives and other advantages of the disclosed input device will be realized and attained by the structure particularly pointed out in the written description and claims thereof as well as the appended drawings.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

Figure 1:
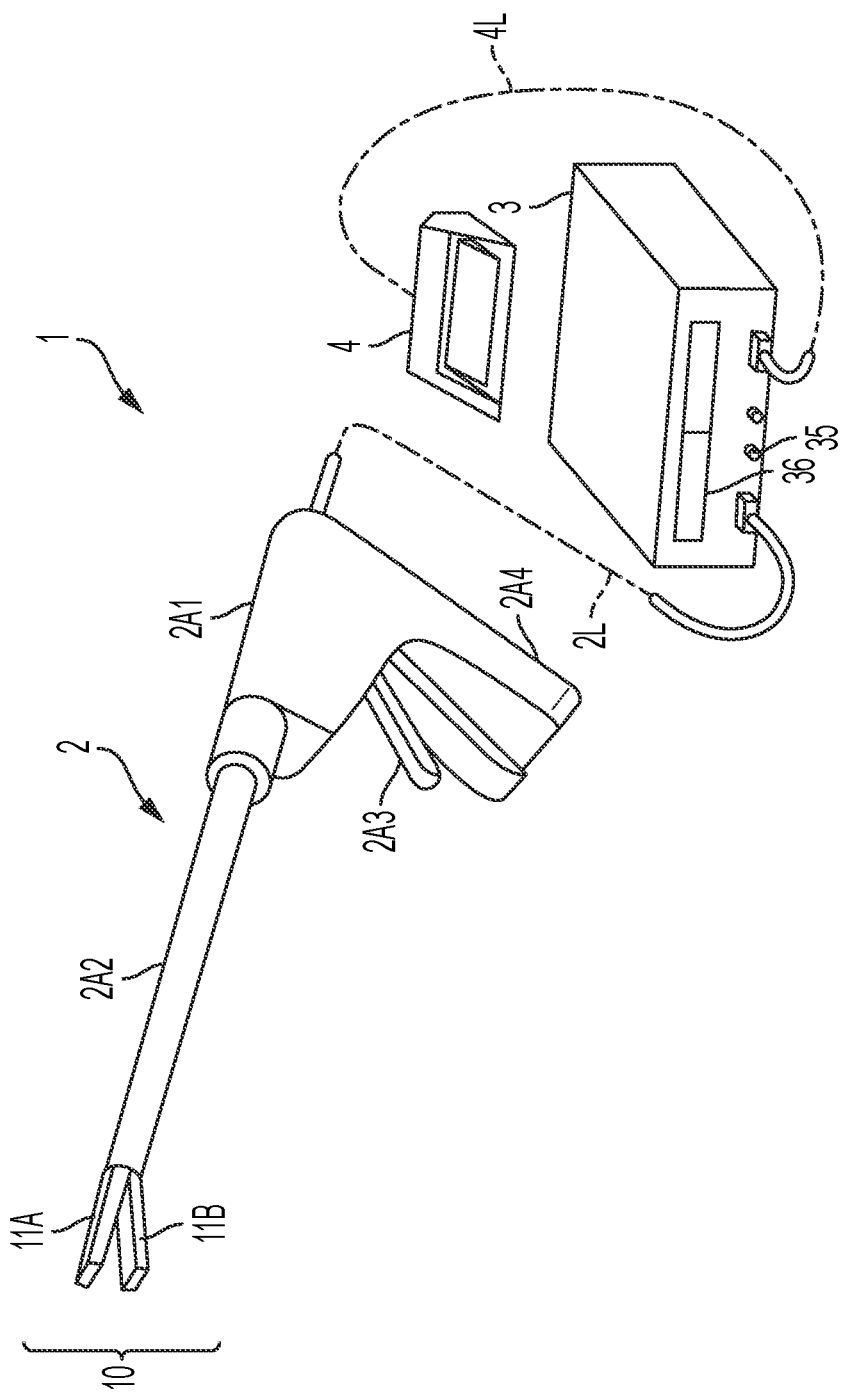
FIG. 1 shows a schematic of a medical device for heating a tissue, in accordance with some embodiments.

Throughout all of the drawings, dimensions of respective constituent elements are appropriately adjusted for clarity. For ease of viewing, in some instances only some of the named features in the figures are labeled with reference numerals.

DETAILED DESCRIPTION

During electrothermal sealing procedures, a high frequency electric current is applied to the biological tissue to be sealed, such as a blood vessel. The electric current results in localized heating of the tissue causing the tissue to desiccate and denature the tissue. In general, as the impedance increases, the current flowing through the tissue decreases, reducing the rate of desiccation. If the impedance rises too quickly, the desiccation process takes longer because of the smaller current. While it is possible to increase the current as the impedance of the tissue increases, there is a risk of damaging the tissue by overheating with him because charring of the tissue. Moreover, increasing the current as the impedance increases requires increasing the voltage applied across the tissue thereby making the procedure inefficient and slow. In other words, an optimum rate of increase in impedance of the tissue depends on the size of the tissue. Because the rate of increase in impedance is controlled by the rate of increase of the voltage applied across the tissue, the rate of increase of the voltage applied across the tissue is carefully modulated to improve the efficiency and speed of the sealing process.

Many parameters related to the electrothermal sealing procedures can be monitored in-process, correlated to the size of the tissue to which the electrothermal sealing procedures is being applied, and any resulting updated tissue size (relative to the initial or first-instance determination of tissue size) can be used to refine the high frequency electric current used during the electrothermal sealing procedures. As the current is applied, the impedance (Z) of the tissue increases at a rate that is dependent on the size of the tissue (where $\dot{Z}$ represents the rate of increase in impedance (Z)). Thus, in one example, during electrothermal sealing procedures, the rate of increase in impedance for larger tissue ($\dot{Z}_L$) is observed to be lower than the rate of increase in impedance for a smaller tissue ($\dot{Z}_S$), e.g., $\dot{Z}_L < \dot{Z}_S$. In another example, during electrothermal sealing procedures, the value of impedance for smaller tissue ($Z_S$) is observed to be higher than the value of impedance for a larger tissue ($Z_L$), e.g., $Z_L < Z_S$. In a still further example, during electrothermal sealing procedures, the value of integrated power (delivered during the procedure) for larger tissue ($\int P_L$) is observed to be higher than the value of integrated power (delivered during the procedure) for a smaller tissue ($\int P_S$), e.g., $\int P_S < \int P_L$. Without wishing to be bound by theory, the relative values of these parameters is likely because the larger tissue has more moisture and greater electrolyte content, and thus takes longer to desiccate. As used here for describing the size of blood vessels, small refers to blood vessels having a diameter of 0 mm to 3 mm, medium refers to blood vessels having a diameter of 3 mm to 5 mm, and large refers to blood vessels having a diameter of 5 mm to 7 mm.

Accordingly, a method for sealing a biological tissue using high frequency electrical energy may include monitoring one or more of the above-noted in-process parameters associated with heating or desiccating the tissue and changing, updating or otherwise modulating the application of high frequency electrical energy to the tissue based on a second determination of the tissue size following a first initial determination.

High frequency, as used herein, refers to a frequency in a range from about 100 kHz to about 5 MHz. Thus, depending on the specific application, a device (such as a device for electrothermal sealing) may supply electrical energy to the tissue by applying a voltage at a frequency of, e.g., 100 kHz, 150 kHz, 200 kHz, 250 kHz, 300 kHz, 350 kHz, 400 kHz, 450 kHz, 500 kHz, 600 kHz, 700 kHz, 800 kHz, 900 kHz, 1000 kHz, 1500 kHz, 2000 kHz, 2500 kHz, 3000 kHz, 3500 kHz, 4000 kHz, 4500 kHz, 5000 kHz, or any frequency between any two of these frequencies.

In an aspect of the present disclosure, a system for sealing a tissue using high frequency electrical energy provided to a tissue is disclosed. The system may include an energy source configured to generate high frequency electrical energy and an end effector operably connected to the energy source and configured to provide the high frequency electrical energy to the tissue. The system further includes a controller operably connected to the energy source and configured to determine an initial impedance of the tissue. The controller then determines a first-instance size of the tissue based on the initial impedance. The controller than causes the electrical energy supplied to the tissue to be first-instance modulated based on the first-instance size of the tissue so as to desiccate the tissue. A second-instance size of the tissue after the voltage has been applied is determined based on an output parameter associated with the desiccation of the tissue. Example output parameters include impedance (Z), rate of increase in impedance ($\dot{Z}$), value of integrated power (delivered during the procedure) ($\int P$), or combinations of these parameters. The electrical energy supplied to the tissue is second-instance modulated based on the second-instance size of the tissue so as to seal the tissue.

The term "patient," as used herein, comprises any and all organisms and includes the term "subject." A patient can be a human or an animal.

Medical Device for Heating Tissue

FIG. 1 shows a schematic of a medical device for heating a tissue, in accordance with an embodiment of the present disclosure. As shown in FIG. 1, the medical device 1 for sealing a tissue is provided with an instrument 2, a controller 3 having a processor, and an actuation switch 4. The instrument 2 may include, for example, a clamp used for grasping a biological tissue during an electrosurgical procedure.

The treatment instrument 2 has a grip 2A1, a shaft 2A2, and a treatment section constituted by an end-effector 10 such as, for example, an openable or pivoting pair of grasping sections (including a first grasping section 11A and a second grasping section 11B) for grasping living tissue (LT) to perform treatment. The grasping sections as whole are also referred to herein as the "treatment portion" or the "treatment section" of the medical instrument. Note that, hereinafter, at time of mentioning each of components having a same function and having reference numerals with A and B attached to ends of the reference numerals, respectively, the symbol A or B may be omitted. For example, each of the first grasping section 11A and the second grasping section 11B may be referred to as the grasping section.

The grip 2A1 is connected to the controller 3 via a cable 2L. The grip 2A1 has an opening/closing actuator 2A3, such as a trigger, for a surgeon to operate opening and closing of the treatment section in such a shape that the surgeon can easily clasp the tissue. The opening/closing actuator 2A3 is arranged at one end of the grip 2A1 and is integrated with the treatment section to transmit operation of the opening/closing actuator 2A3 to the treatment section. On the other side of the grip 2A1, a grasping portion 2A4 is provided for a clinician to grasp when operating the instrument 2.

Figure 2:
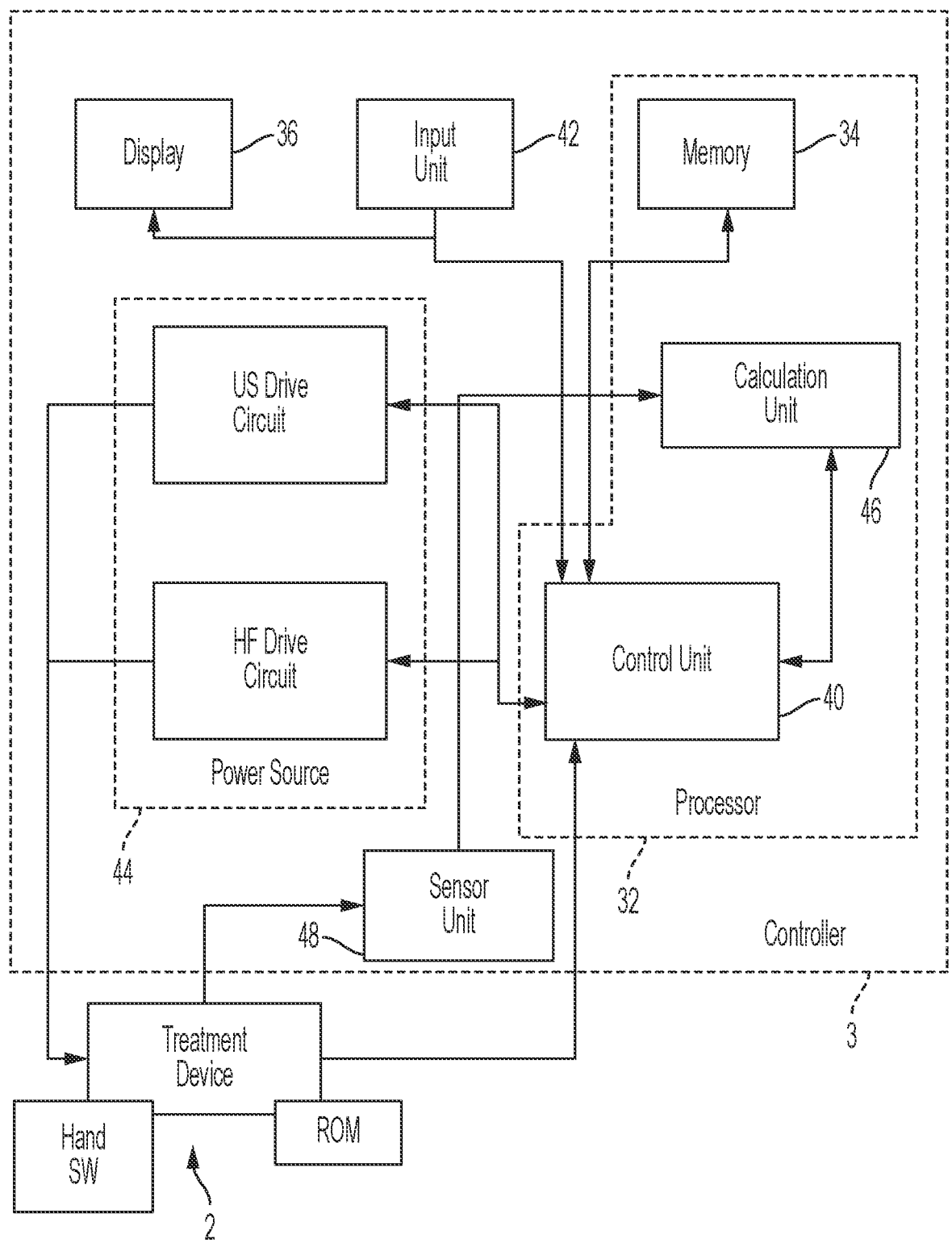
FIG. 2 shows a schematic of a controller in accordance with embodiments.

FIG. 2 shows a schematic of a controller in accordance with an embodiment of the present disclosure. The controller 3 may include a processor 32, a display 36, an input unit 42, a sensor unit 48, and a power source 44.

The processor 32 may include a memory 34, a calculation unit 46 and a control unit 40. The calculation unit 46 and the control unit 40 are formed of an integrated circuit including a CPU (Central Processing Unit), an ASIC (Application Specific Integrated Circuit) or an FPGA (Field Programmable Gate Array). The calculation unit 46 and the control unit 40 may be formed a single integrated circuit, or may be formed of a plurality of integrated circuits.

The control unit 40 is configured to control the power source 44 and the display 36 based on the commands provided by the processor 32 using the parameters computed by the calculation unit 46.

The display 36 that displays treatment conditions and the like, and a setting operation section 35 for the surgeon to set the treatment conditions and the like, are on a front panel of the controller 3. In some embodiments, the controller 3 may be connected to a switch 4 via a cable 4L. The switch 4 may be used by the clinician performing the procedure for controlling power applied to the instrument, for example, between sealing two different vessels.

In some embodiments, various parameters used for determining an impedance of the living tissue such as, for example, the size of the tissue, the type of the tissue, or any other factors that determine the impedance of the tissue may be stored in memory 34, e.g., in a look-up table stored in the memory 34. The look-up table may include the values of the corresponding parameters for different treatment portions. For example, the look-up table may include the parameters for muscle tissue, adipose tissue, blood vessels, intestinal wall, or other tissue types. Also for example, the look-up table may include sized-based variations in parameters, such as the impedance (Z), rate of increase in impedance ($\dot{Z}$), and value of integrated power (delivered during the procedure) ($\int P$) for different treatment portions based on the size of the treatment portion. Such sized-based variations in parameters may be quantized based on predetermined small, medium, or large size characteristics of the treatment portion, may be quantized based on predetermined size ranges of the treatment portion, or may be on a continuum based on size of the treatment portion.

The calculation unit 46 is configured to compute the impedance (Z) at, before or during heating of the tissue, as well as other parameters that are needed for computing the impedance.

The sensor unit 48 is configured to determine an output parameter associated with the desiccation of the tissue. For example, the sensor unit 48 may be configured to determine a rate of increase in impedance ($\dot{Z}$) of the tissue during the process of desiccation in some embodiments. Additionally or alternately, the sensor unit 48, in some embodiments, may be configured to determine an impedance (Z) of the tissue during or after the desiccation process. The sensor unit 48 may also be configured to determine the total energy supplied to the tissue over a certain period of time by, for example, integrating the power output by the treatment instrument 2 over the time for which the power was output, i.e., a value of integrated power ($\int P$).

In some embodiments, the calculation unit 46 is configured to determine a size of the tissue based on input received from the control unit 40 and/or the sensor unit 48. For example, in some embodiments, the calculation unit 46 may determine the size of the tissue based on an output parameter measured by the sensor unit 48. The size of the tissue may be estimated based on the output parameter using a mathematical formula or by using a look-up table which may include pre-calculated values for tissue sizes for certain values of output parameters, either on a quantized-basis or a continuum-basis.

Figure 3:
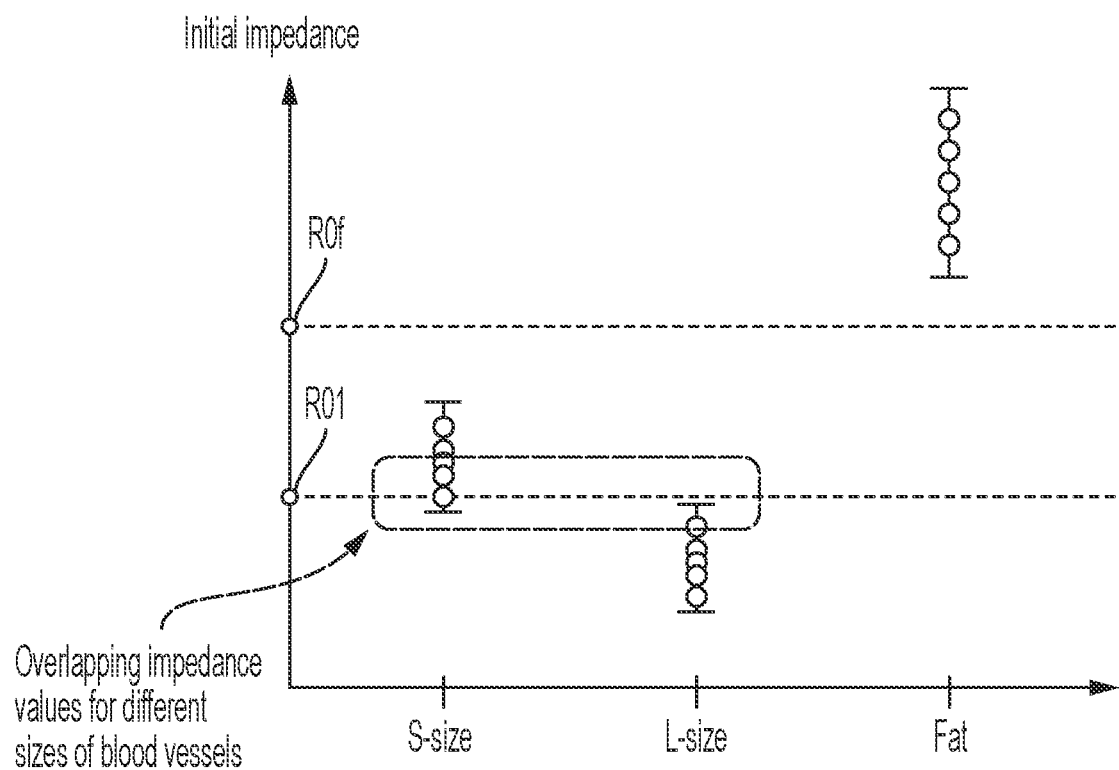
FIG. 3 illustrates an example of measured initial impedance as a function of size of blood vessel.

FIG. 3 is a graph illustrating initial impedance values (Z) (on a relative-basis) for different sizes of blood vessels. Such graph may be used for creating a look-up table for determining the size of tissue based on impedance of the tissue.

Referring back to FIG. 2, in some embodiments, the power source 44 is operatively coupled to a processor 32 which controls the application of power to the instrument 2 by the power source 44 so as to appropriately modulate the electrical energy supplied or provided to the tissue during the sealing procedure.

To control the power input to the instrument 2, the processor 32 may determine an in-process impedance of the tissue during the procedure and determine whether the in-process impedance has reached a certain threshold for a given cycle, for example, based on an output parameter measured by the sensor unit 48. In addition, the processor 32 may determine a desiccation state of the tissue based on the output parameter measured by the sensor unit 48.

In some embodiments, the processor 32 controls the electrical energy supplied to the treatment instrument 2 by controlling the output voltage of the drive circuit(s). Thus, the processor 32 may cause the power source 44 to increase or decrease the voltage applied by the treatment instrument 2 across the tissue as well as change the rate of the increase or decrease in the applied voltage. Additionally, the processor 32 may cause the power source 44 to stop the application of voltage by the treatment instrument 2.

For example, in some embodiments, before the start of the sealing procedure or in conjunction with the beginning of the sealing procedure, the processor 32 may control the power source to apply a constant power to a tissue for a certain period of time such as, for example, about 10 ms, about 20 ms, about 30 ms, about 40 ms, about 50 ms, about 60 ms, about 70 ms, about 80 ms, about 90 ms, about 100 ms, about 120 ms, about 140 ms, about 160 ms, about 180 ms, about 200 ms, about 250 ms, about 300 ms, about 400 ms, or any other amount of time between any two of these values. The sensor unit 48 may then measure the impedance (Z) of the tissue and the calculation unit 46 may estimate a first-instance size of the tissue based on the initially measured impedance ($Z_i$).

The processor 32 may then control the power source 44 to modulate or increase, in the first instance, the electrical energy supplied to the tissue by increasing the voltage applied across the tissue to a first threshold. The first threshold may be determined by the calculation unit 46 based on the estimated first-instance size of the tissue. As discussed herein, the rate at which the applied voltage is increased may be determined by the processor 32 based on the first-instance size in some embodiments. Thus, the amount of time needed for the voltage across the tissue to increase to the first threshold may be dependent on the first-instance size of the tissue. For example, the first-instance increase in the voltage applied across the tissue may be performed over a period of about 10 ms, about 20 ms, about 30 ms, about 40 ms, about 50 ms, about 60 ms, about 70 ms, about 80 ms, about 90 ms, about 100 ms, about 120 ms, about 140 ms, about 160 ms, about 180 ms, about 200 ms, about 250 ms, about 300 ms, about 400 ms, about 500 ms, about 600 ms, about 700 ms, about 800 ms, about 900 ms, about 1000 ms, about 1100 ms, about 1200 ms, about 1300 ms, about 1400 ms, about 1500 ms, about 1600 ms, about 1700 ms, about 1800 ms, about 1900 ms, about 2000 ms, about 2200 ms, about 2400 ms, about 2600 ms, about 2800 ms, about 3000 ms, about 3500 ms, about 4000 ms, about 5000 ms, or any other amount of time between any two of these values.

Once the voltage applied across the tissue reaches the first threshold, the processor 32 may then determine a second-instance size of the tissue based on, for example, any one output parameter or combination of output parameters measured by the sensor unit 48. The output parameter may be any of the output parameters disclosed herein. For example, the output parameter may be an impedance (Z) of the tissue when the voltage across the tissue is at the first threshold, a rate of increase of the impedance ($\dot{Z}$) during the time the voltage across the tissue is increased to the first threshold, or the total electrical energy supplied to the tissue during the time the voltage across the tissue is increased to the first threshold, i.e., a value of integrated power ($\smallint P$). Once the sensor unit 48 measures the output parameter, the calculation unit 46 may estimate the second-instance size of the tissue, e.g., using a mathematical formula or a look-up table as disclosed elsewhere herein.

The processor 32 may then control the power output by the power source 44 based on the second-instance size of the tissue so as to complete the sealing process. For example, where the second-instance size is determined to be the same as the first-instance size, the processor 32 may cause the power source 44 to continue to supply electrical energy to the tissue using the same input parameters as that used prior to determining the second-instance size.

Alternately, if the second-instance size is determined to be different than the first-instance size, the processor 32 may cause the power source 44 to change the parameters for supplying electrical energy to tissue. For example, the processor 32 may cause the power source 44 to increase or decrease the voltage applied across the tissue, to change the rate of increase or decrease of the applied voltage, to increase or decrease an amount of total electrical energy supplied to the tissue during the time the voltage is applied across the tissue, i.e., a value of integrated power ($\smallint P$), or a combination of such changes.

The change in the input parameters used for completing the sealing process after determining the second-instance size of the tissue may be based on the second-instance size, and in particular, based on whether the second-instance size is determined to be greater than or smaller than the first-instance size.

Figure 4:
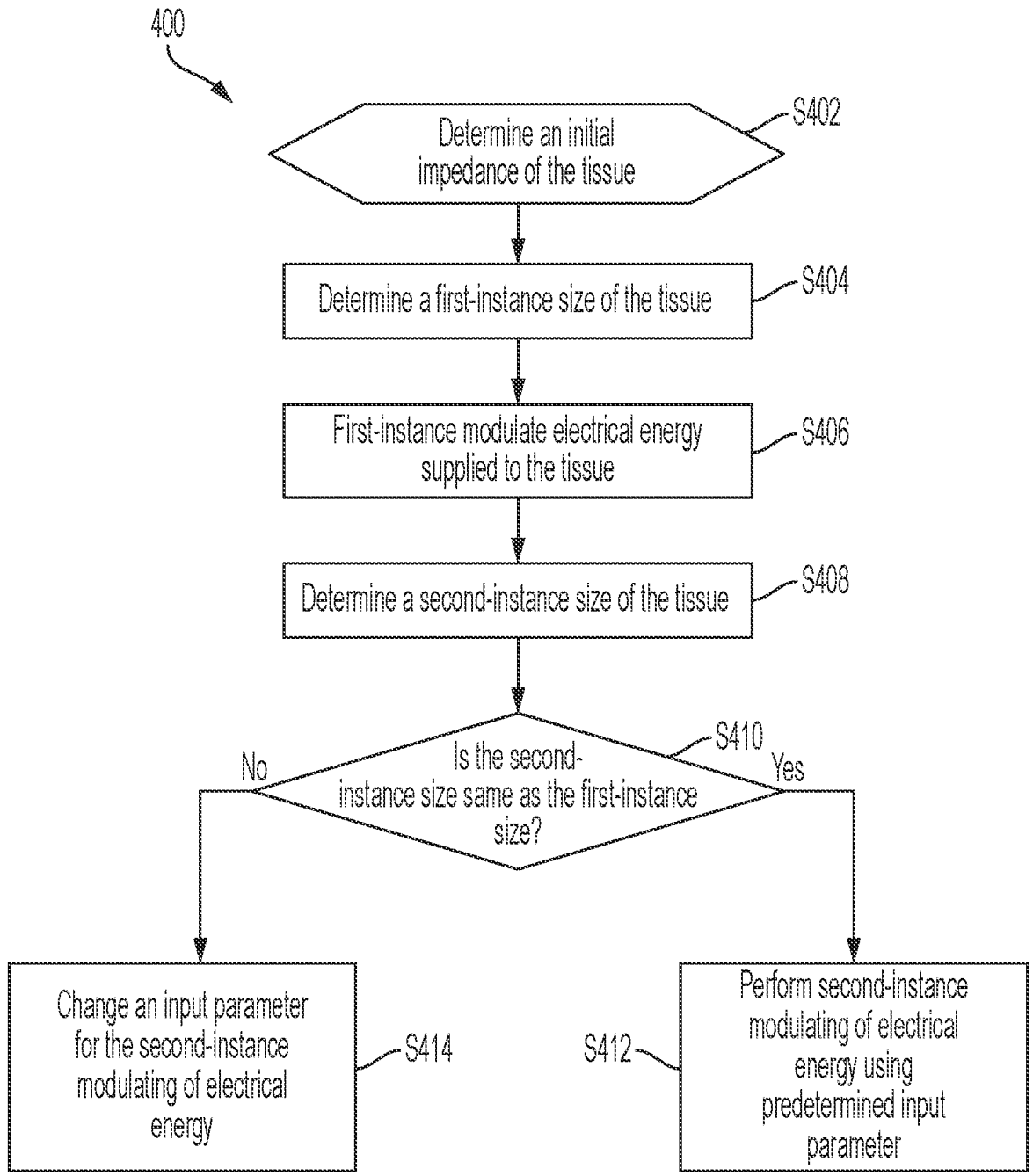
FIG. 4 illustrates a flow chart for a method of sealing a living tissue in accordance with some embodiments.

In another aspect, the present disclosure relates to a method for sealing a living tissue using high frequency electrical energy. FIG. 4 illustrates a flow chart for a method of sealing a living tissue in accordance with some embodiments.

The method 400 may include determining, at S402, an initial impedance ($Z_i$) of the tissue. The initial impedance ($Z_i$) may be determined by supplying constant power to the tissue for a predetermined period of time and measuring the ratio of voltage to current during that period of time. The constant power may be applied for a period of, for example, about 10 ms, about 20 ms, about 30 ms, about 40 ms, about 50 ms, about 60 ms, about 70 ms, about 80 ms, about 90 ms, about 100 ms, about 120 ms, about 140 ms, about 160 ms, about 180 ms, about 200 ms, about 250 ms, about 300 ms, about 400 ms, or any other amount of time between any two of these values.

A first-instance size of the tissue is determined, at S404, based on the initial impedance ($Z_i$). As discussed elsewhere herein, the first-instance size of the tissue may be determined based on, for example, a mathematical formula or a look-up table.

At S406, the electrical energy supplied to the tissue is first-instance modulated based on the first-instance size of the tissue so as to desiccate the tissue. In some embodiments, the first-instance modulating of electrical energy supplied to the tissue may include increasing a voltage applied across the tissue to a first threshold. Similarly, the first threshold may be determined based on the first-instance size determined at S404. Additionally or alternatively, the rate of increasing the voltage applied across the tissue may be based on the first-instance size and the amount of total electrical energy supplied to the tissue during the time the voltage is applied across the tissue, i.e., a value of integrated power ($\smallint P$), may be based on the first-instance size.

In some embodiments, a desiccation state of the tissue may be determined during the first-instance modulating of the electrical energy. For example, an impedance (Z) of the tissue may be determined during the first-instance modulating of the electrical energy, and a desiccation state may be determined based on the impedance using, for example, a look-up table. For example, based on the first-instance size of the tissue, a tissue may be considered dry if the impedance of the tissue is equal to or greater than a drying threshold for that size of tissue.

In some embodiments, the parameters associated with the first-instance modulating of the electrical energy may be changed based on the desiccation state of the tissue. For example, if it is determined that the tissue is not dry based on the measured impedance of the tissue during the first-instance modulating of the electrical energy supplied to the tissue, the first-instance modulating may be prolonged, the first threshold may be increased, the rate of increasing the voltage during the first-instance modulating may be increased, or the amount of total electrical energy supplied to the tissue during the time the voltage is applied across the tissue, i.e., a value of integrated power (∫P), may be increased.

At S408, a second-instance size of the tissue after the voltage has been applied is determined based on an output parameter associated with the desiccation of the tissue. In some embodiments, the output parameter may include an impedance of the tissue after the first-instance modulating of the electrical energy supplied to the tissue or a rate of increase in impedance of the tissue during the first-instance modulating of the electrical energy supplied of the tissue.

In some embodiments, the output parameter may include an amount of electrical energy supplied to the tissue during the first-instance modulating of the electrical energy supplied to the tissue. The amount of electrical energy supplied to the tissue during the first-instance modulating of the electrical energy may be determined by integrating the power input to the tissue over the time for which the power is input to the tissue. As discussed elsewhere herein, the first-instance modulating of electrical energy may be performed over a period of about 10 ms, about 20 ms, about 30 ms, about 40 ms, about 50 ms, about 60 ms, about 70 ms, about 80 ms, about 90 ms, about 100 ms, about 120 ms, about 140 ms, about 160 ms, about 180 ms, about 200 ms, about 250 ms, about 300 ms, about 400 ms, about 500 ms, about 600 ms, about 700 ms, about 800 ms, about 900 ms, about 1000 ms, about 1100 ms, about 1200 ms, about 1300 ms, about 1400 ms, about 1500 ms, about 1600 ms, about 1700 ms, about 1800 ms, about 1900 ms, about 2000 ms, about 2200 ms, about 2400 ms, about 2600 ms, about 2800 ms, about 3000 ms, about 3500 ms, about 4000 ms, about 5000 ms, or any other amount of time between any two of these values.

At S410, the second-instance size of the tissue determined at S408 is compared to the first-instance size of the tissue determined at S404. If it is determined at S410 that the second-instance size is the same as the first instance size (YES), the sealing process may be completed, at S412, based on the same input parameters used during the first-instance modulating of electrical energy.

On the other hand, if it is determined at S410 that the second-instance size of the tissue determined at S408 is different from the first-instance size of the tissue determined at S404, the sealing process is completed at S414 by changing the input parameters used for the second-instance modulating of the electrical energy.

For example, if it is determined that the second-instance size is greater than the first-instance size, one or more of the input parameters is increased for the second-instance modulating of the electrical energy. On the other hand, if it determined that the second-instance size is smaller than the first-instance size, one or more of the input parameters is decreased for the second-instance modulating of the electrical energy.

EXAMPLES

The following examples demonstrate the behavior of in-process impedance, rate of change of in-process impedance, and in-process integrated power delivered to the tissue during electrothermal sealing procedures. In the examples, the behavior of these in-process parameters is shown for (a) when the first-instance size of the tissue has been determined as large when, in fact, the first-instance size of the tissue is small, i.e., a small tissue is mischaracterized as a large tissue in the first instance, and (b) when the first-instance size of the tissue has been determined as large when, in fact, the first-instance size of the tissue is large, .e., a large tissue is correctly characterized as a large tissue in the first instance.

Differences and comparisons in the behavior of in-process parameter can be seen by comparing the provided graphs, particularly in the transition region between the Phase 2 and the Phase 3 portions of the electrothermal sealing procedures. The Phase 2 portion of the electrothermal sealing procedure occurs after Phase 1 (in which constant power control is applied at the initiation of the sealing procedure to determine an initial impedance of the tissue) and, in the Phase 2 portion, the voltage applied to the tissue is increased to the value that was determined based on the first-instance size of the tissue. The Phase 3 portion of the electrothermal sealing procedure occurs after Phase 2 and, in the Phase 3 portion, the tissue is treated for a period of time with a constant value of voltage, where the constant value of voltage is based on the first-instance size of the tissue. By understanding and detecting these in-process parameters and understanding their size-based behavior as compared to baseline size-based behavior, one can determine if a first-instance size of the tissue was correct and, if necessary, perform a procedure to re-determine the size of the tissue, i.e., determine a second-instance size, and, based on that second-instance size, change the size-based inputs and parameters to be used in the electrothermal sealing procedure on a going-forward basis, such as until sealing of the tissue is complete.

Additionally, it is understood that, when a value of impedance of the biological tissue reaches a minimum value, that is an indication that the tissue is dry. Typically, during the electrothermal sealing procedure, the transition from Phase 2 to Phase 3 occurs upon an increase of about 20Ω in the minimum value of impedance, or within 3 seconds of such an increase.

Figure 5A:
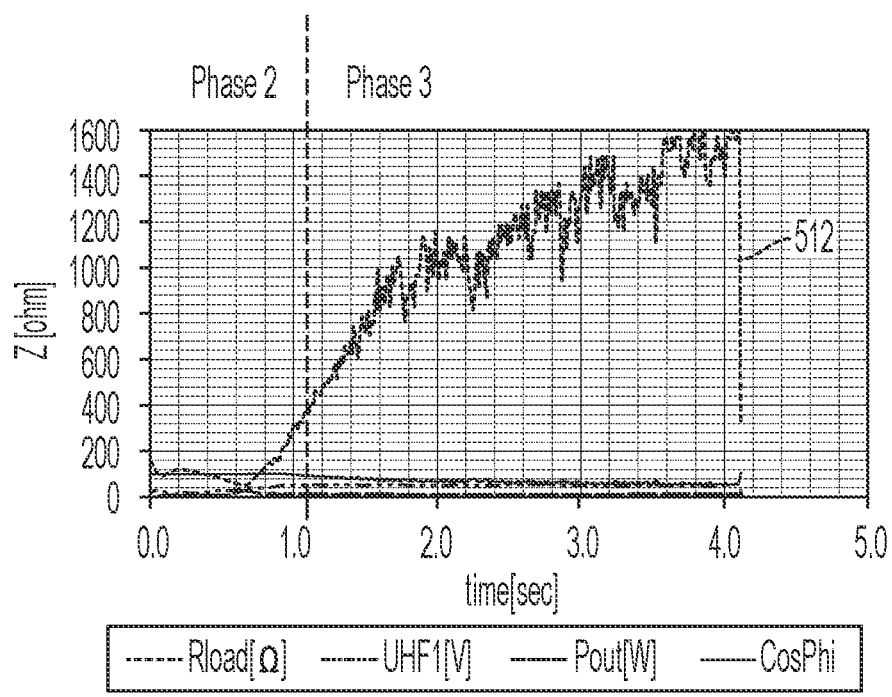
FIGS. 5A and 5B are graphs showing impedance (in ohms) as a function of time (in seconds) in example embodiments in which the size of a tissue is re-determined during the electrothermal sealing procedure based on the rate of change of the in-process impedance (ohms/sec) of the tissue.
Figure 5B:
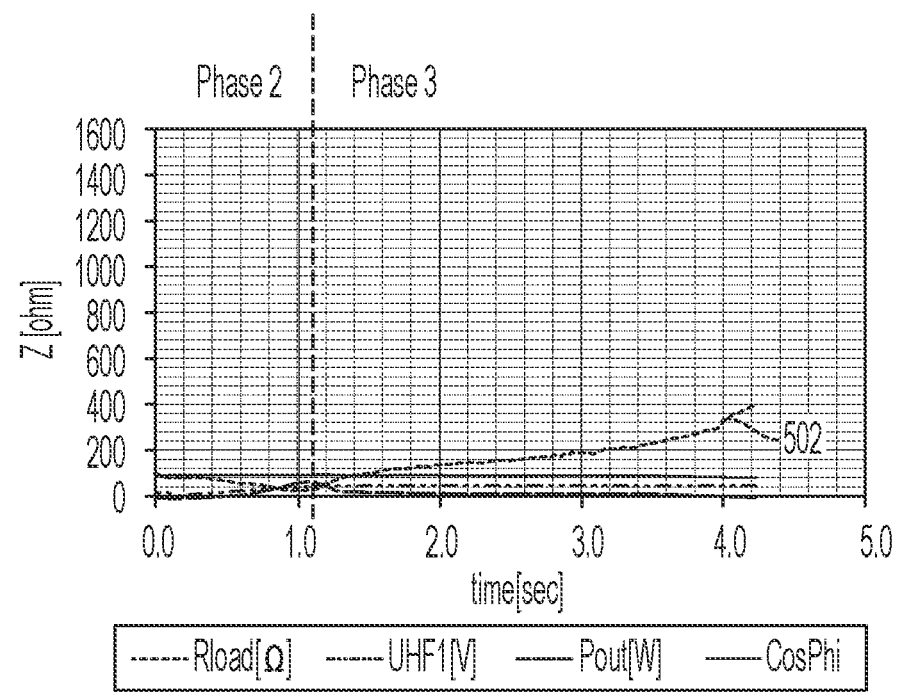

FIGS. 5A and 5B are graphs showing impedance (in ohms) as a function of time (in seconds) in example embodiments in which the size of a tissue is re-determined during the electrothermal sealing procedure based on the rate of change of the in-process impedance of the tissue. In FIG. 5A, the first-instance size of the tissue has been determined as large when, in fact, the first-instance size of the tissue is small, i.e., a small tissue is mischaracterized as a large tissue in the first instance. In FIG. 5B, the first-instance size of the tissue has been determined as large when, in fact, the first-instance size of the tissue is large, .e., a large tissue is correctly characterized as a small tissue in the first instance.

Turning to FIG. 5B, the rate of change of the in-process impedance of the tissue (in ohm/sec (Ω/s)) is shown at 502. Here, the large tissue is correctly characterized as a large tissue in the first instance and the rate of change of the in-process impedance of the tissue 502 after the transition to Phase 3 is substantially constant and has a value, in this example, of 250 Ω/s. In general, where the large tissue is correctly characterized as a large tissue in the first instance, the rate of change of the in-process impedance of the tissue in Phase 3 is less than 400 Ω/s, typically between 100 Ω/s to 400 Ω/s. In general, where a small tissue is correctly characterized as a small tissue in the first instance, the rate of change of the in-process impedance of the tissue in Phase 3 is greater than 400 Ω/s, typically between 400 Ω/s to 600 Ω/s.

Turning to FIG. 5A, the rate of change of the in-process impedance of the tissue (in ohm/sec (Ω/s)) is shown at 512. Here, the small tissue is mischaracterized as a large tissue in the first instance. Also, while the rate of change of the in-process impedance of the tissue 512 in Phase 3 is substantially constant for a beginning portion of time, i.e. the first 1 sec of Phase 3, the rate of change of the in-process impedance of the tissue 512 does change its rate thereafter, and is more scattered (or noisy). Furthermore, the rate of change of the in-process impedance of the tissue 512 in Phase 3 for the beginning portion of time is significantly higher than that for the example in FIG. 5B. In the size mischaracterized example in FIG. 5A, the rate of change of the in-process impedance of the tissue 512 in Phase 3 has a value (in the beginning portion of time) of 1100 Ω/s. In generally, where the small tissue is mischaracterized as a large tissue in the first instance, the rate of change of the in-process impedance of the tissue in Phase 3 is about double the in-general value of the rate of change of the in-process impedance of the tissue in Phase 3 where the large tissue is correctly characterized as a large tissue in the first instance. Also in general, where the small tissue is mischaracterized as a large tissue in the first instance, the rate of change of the in-process impedance of the tissue in Phase 3 is greater than 1000 Ω/s, typically between 1000 Ω/s to 1500 Ω/s.

Figure 6A:
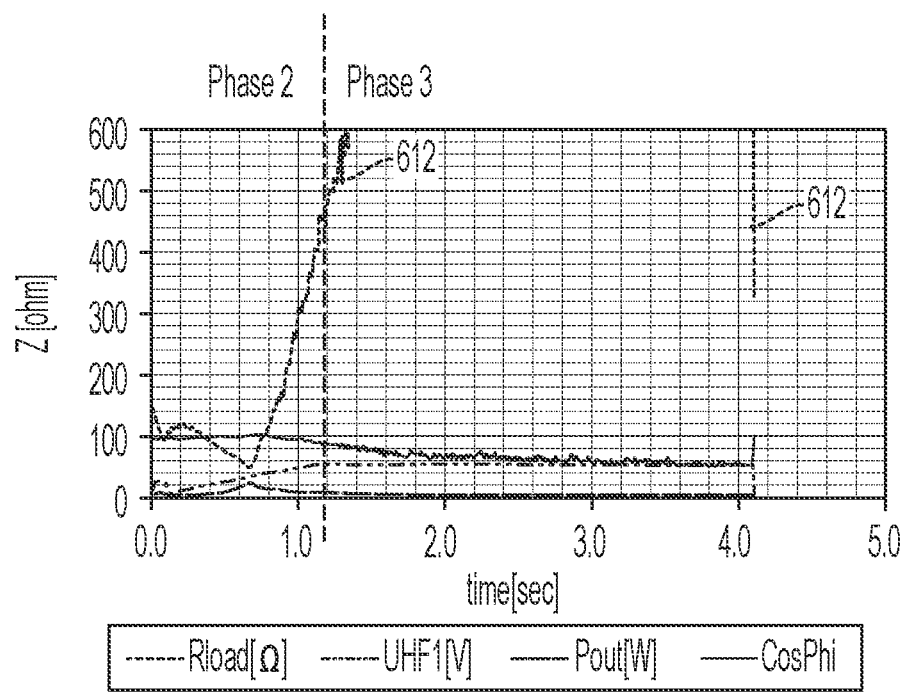
FIGS. 6A and 6B are graphs showing impedance (in ohms) as a function of time (in seconds) in example embodiments in which the size of a tissue is re-determined during the electrothermal sealing procedure based on the value of in-process impedance (in ohms) of the tissue.
Figure 6B:
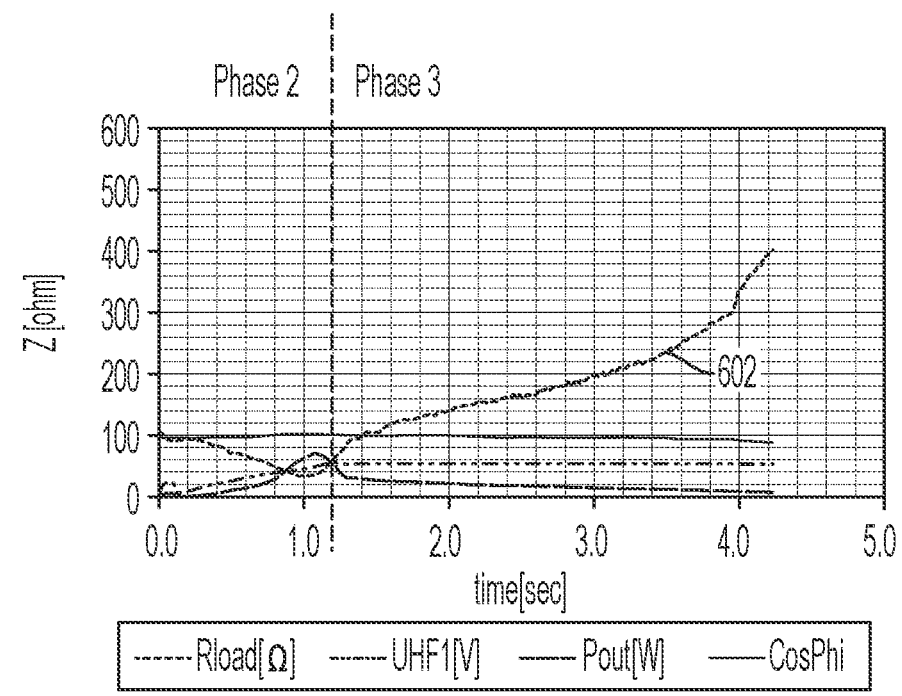

FIGS. 6A and 6B are graphs showing impedance (in ohms) as a function of time (in seconds) in example embodiments in which the size of a tissue is re-determined during the electrothermal sealing procedure based on the value of in-process impedance of the tissue. In FIG. 6A, the first-instance size of the tissue has been determined as large when, in fact, the first-instance size of the tissue is small, i.e., a small tissue is mischaracterized as a large tissue in the first instance. In FIG. 6B, the first-instance size of the tissue has been determined as large when, in fact, the first-instance size of the tissue is large, .e., a large tissue is correctly characterized as a large tissue in the first instance.

Turning to FIG. 6B, the value of the in-process impedance of the tissue (in ohm (Ω)) is shown at 602. Here, the large tissue is correctly characterized as a large tissue in the first instance and the value of the in-process impedance of the tissue 602 at the transition from Phase 2 to Phase 3 has a value, in this example, of 67Ω. In general, where the large tissue is correctly characterized as a large tissue in the first instance, the value of the in-process impedance of the tissue at the transition from Phase 2 to Phase 3 is less than 100Ω, typically between 60Ω to 80Ω. In general, where the small tissue is correctly characterized as a small tissue in the first instance, the value of the in-process impedance of the tissue at the transition from Phase 2 to Phase 3 is greater than 80Ω.

Turning to FIG. 6A, the value of the in-process impedance of the tissue (in ohm (Ω) is shown at 612 (note that line 612 increases and leaves the graphed range shortly after starting Phase 3, but the returns to the graphed range later in Phase 3). Here, the small tissue is mischaracterized as a large tissue in the first instance and the value of the in-process impedance of the tissue 612 at the transition from Phase 2 to Phase 3 is significantly higher than that for the example in FIG. 6B. In the size mischaracterized example in FIG. 6A, the value of the in-process impedance of the tissue 612 at the transition from Phase 2 to Phase 3 is 366Ω. In generally, where the small tissue is mischaracterized as a large tissue in the first instance, the value of the in-process impedance of the tissue at the transition from Phase 2 to Phase 3 is about four-times the in general value of the in-process impedance of the at the transition from Phase 2 to Phase 3 where the large tissue is correctly characterized as a large tissue in the first instance. Also in general, where the small tissue is mischaracterized as a large tissue in the first instance, the value of the in-process impedance of the tissue in at the transition from Phase 2 to Phase 3 is greater than 200 Ω/s, typically between 200Ω to 500Ω.

Figure 7A:
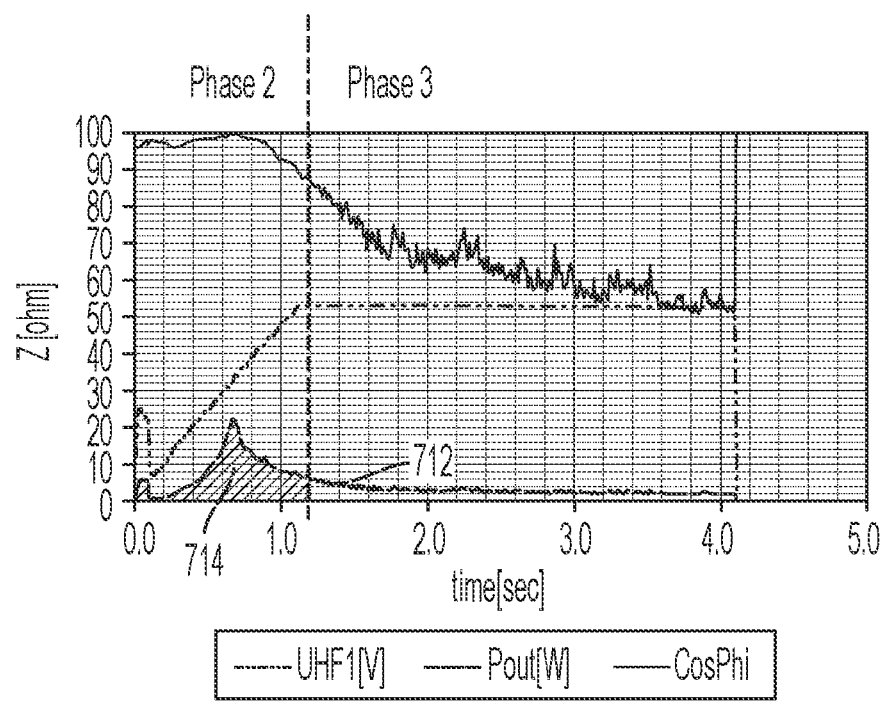
FIGS. 7A and 7B are graphs showing impedance (in ohms) as a function of time (in seconds) in example embodiments in which the size of a tissue is re-determined during the electrothermal sealing procedure based on the value of in-process integrated power (in Joules) delivered to the tissue.
Figure 7B:
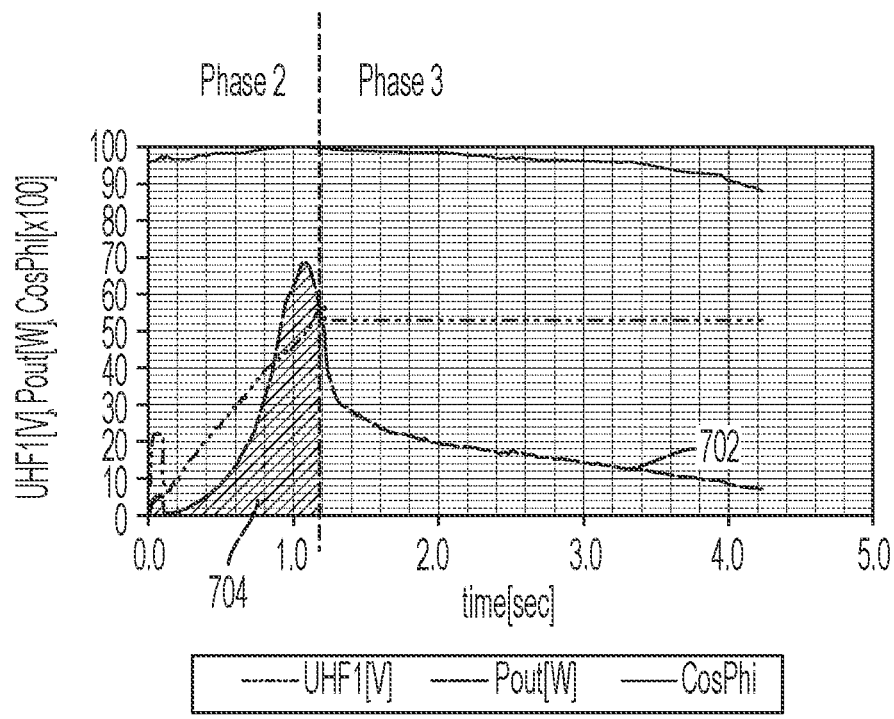

FIGS. 7A and 7B are graphs showing the value of the in-process power delivered to the tissue (in watts (W)) as a function of time (in seconds) in example embodiments in which the size of a tissue is re-determined during the electrothermal sealing procedure based on the value of in-process integrated power delivered to the tissue. In FIG. 7A, the first-instance size of the tissue has been determined as large when, in fact, the first-instance size of the tissue is small, i.e., a small tissue is mischaracterized as a large tissue in the first instance. In FIG. 7B, the first-instance size of the tissue has been determined as large when, in fact, the first-instance size of the tissue is large, i.e., a large tissue is correctly characterized as a large tissue in the first instance.

Turning to FIG. 7B, the value of the in-process power delivered to the tissue (in watts (W)) is shown at 702. The value of integrated power (delivered during the procedure) (∫P) (in Joules (J)) is determined by taking the area under the curve, i.e., area under 702. If on a time basis, the value of integrated power is determined for a specific time period, such as during Phase 2 or from 100 msec to 3 sec. Here, the large tissue is correctly characterized as a large tissue in the first instance and the value of integrated power (delivered during the procedure) (∫P) for the time period of Phase 2 is area 704 (shown as hatching in FIG. 7B) and has a value, in this example, of 29.9 J. In general, where the large tissue is correctly characterized as a large tissue in the first instance, the value of integrated power (delivered during the procedure) (∫P) for the time period of Phase 2 is greater than 20 J, typically between 20 J to 50 J.

Turning to FIG. 7A, the value of integrated power (delivered during the procedure) (∫P) (in Joules (J)) is determined by taking the area under the curve, i.e., area under 712. If on a time basis, the value of integrated power is determined for a specific time period, such as during Phase 2 or from 200 msec to 1 sec. Here, the small tissue is mischaracterized as a large tissue in the first instance and the value of integrated power (delivered during the procedure) (∫P) for the time period of Phase 2 is area 714 (shown as hatching in FIG. 7A) and has a value, in this example, of 8.9 J. In generally, where the small tissue is mischaracterized as a large tissue in the first instance, the value of integrated power (delivered during the procedure) (∫P) for the time period of Phase 2 is less than half the in-general value of integrated power (delivered during the procedure) (∫P) for the time period of Phase 2 where the large tissue is correctly characterized as a large tissue in the first instance. Also in general, where the small tissue is mischaracterized as a large tissue in the first instance, the value of integrated power (delivered during the procedure) (∫P) for the time period of Phase 2 is less than 15 J, typically between 5 J to 15 J.

The system and method disclosed herein reduce the time required for sealing a tissue, such as a biological living tissue of a patient, during an electrosurgical procedure. The system and method disclosed herein further reduce the incidence of overheating the tissue during the sealing process, thereby improving patient safety. In addition, by controlling the energy input to the tissue based on the size of the tissue during the sealing process, the system and method disclosed herein improves the efficiency of the process of sealing the tissue.

Although the present invention has been described in connection with the above exemplary embodiments, it will be appreciated by those skilled in the art that additions, deletions, modifications, and substitutions not specifically described may be made without department from the spirit and scope of the invention as defined in the appended claims.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The singular forms "a," "an," and "the" include plural referents unless the context clearly dictates otherwise. Thus, for example, reference to "a plunger component" includes reference to one or more plunger components, and reference to "the magnet" includes reference to one or more magnets.

In one or more aspects, the terms "about," "substantially," and "approximately" may provide an industry-accepted tolerance for their corresponding terms and/or relativity between items, such as from less than one percent to five percent.

As used herein, the term "substantially" refers to the complete or nearly complete extent or degree of an action, characteristic, property, state, structure, item, or result.

It is to be understood that a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 cm" should be interpreted to include not only the explicitly recited values of about 0.5 cm to about 10.0 cm, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this disclosure belongs. Although any methods, devices and materials similar or equivalent to those described herein can be used in the practice or testing of the disclosure, representative methods, devices, and materials are described below.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Many modifications may be made to this configuration without departing from the scope or spirit of the claimed subject matter.

Although the detailed description contains many specifics, these should not be construed as limiting the scope of the subject technology but merely as illustrating different examples and aspects of the subject technology. It should be appreciated that the scope of the subject technology includes some embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method for sealing a biological tissue using high frequency electrical energy, the method comprising:
    determining an initial impedance of the biological tissue;
    determining a first-instance size of the biological tissue based on the initial impedance;
    applying a first-instance electrical energy to the biological tissue, wherein a value of voltage of the first-instance electrical energy and a length of time of application of the first-instance electrical energy are both based on the first-instance size of the biological tissue;
    detecting an in-process parameter during applying the first-instance electrical energy to the biological tissue, wherein the in-process parameter is (i) a value of in-process impedance of the biological tissue, (ii) a rate of change of the in-process impedance of the biological tissue, (iii) a value of in-process integrated power delivered to the biological tissue, or (iv) a combination thereof;
    determining a second-instance size of the biological tissue based on the detected in-process parameter; and
    applying a second-instance electrical energy to the biological tissue, wherein a value of voltage of the second-instance electrical energy and a length of time of application of the second-instance electrical energy are both based on the second-instance size of the biological tissue.

2. The method according to claim 1, wherein, when the first-instance size of the biological tissue based on the initial impedance is large and the value of in-process impedance of the biological tissue is greater than 200Ω, then the second-instance size of the biological tissue is determined as small, and
    wherein the second-instance electrical energy to the biological tissue is different than the first-instance electrical energy to the biological tissue.

3. The method according to claim 1, wherein the in-process parameter is the rate of change of the in-process impedance of the biological tissue.

4. The method according to claim 1, wherein the in-process parameter is the value of in-process integrated power delivered to the biological tissue.

5. The method according to claim 1, wherein, when the second-instance size of the biological tissue is different than the first-instance size of the biological tissue, the second-instance electrical energy to the biological tissue is different than the first-instance electrical energy to the biological tissue.

6. A system for sealing a biological tissue, the system comprising:
    an energy source configured to generate high frequency electrical energy;
    an end effector operably connected to the energy source and configured to provide the high frequency electrical energy to the biological tissue; and
    a controller operably connected to the energy source and configured to:
        determine an initial impedance of the biological tissue;
        determine a first-instance size of the biological tissue based on the initial impedance;
        apply a first-instance electrical energy to the biological tissue, wherein a value of voltage of the first-instance electrical energy and a length of time of application of the first-instance electrical energy are both based on the first-instance size of the biological tissue;
        detect an in-process parameter during applying the first-instance electrical energy to the biological tissue, wherein the in-process parameter is (i) a value of in-process impedance of the biological tissue, (ii) a rate of change of the in-process impedance of the biological tissue, (iii) a value of in-process integrated power delivered to the biological tissue, or (iv) a combination thereof;
        determine a second-instance size of the biological tissue based on the detected in-process parameter; and
        apply a second-instance electrical energy to the biological tissue, wherein a value of voltage of the second-instance electrical energy and a length of time of application of the second-instance electrical energy are both based on the second-instance size of the biological tissue.

7. The system according to claim 6, wherein the controller is configured to apply the second-instance electrical energy is to the biological tissue until sealing of the tissue is complete.

8. The system according to claim 6, wherein, when the second-instance size of the biological tissue is different than the first-instance size of the biological tissue, the second-instance electrical energy to the biological tissue is different than the first-instance electrical energy to the biological tissue.

9. The system according to claim 6, wherein, when the second-instance size of the biological tissue is the same as the first-instance size of the biological tissue, the second-instance electrical energy to the biological tissue is the same as the first-instance electrical energy to the biological tissue.

10. The system according to claim 6, wherein the in-process parameter is the value of in-process impedance of the biological tissue.

11. The system according to claim 6, wherein the in-process parameter is the rate of change of the in-process impedance of the biological tissue.

12. The system according to claim 6, wherein the in-process parameter is the value of in-process integrated power delivered to the biological tissue.

13. A controller for a device for sealing a biological tissue, the controller being operably connected to an energy source and configured to:
- determine an initial impedance of the biological tissue;
- determine a first-instance size of the biological tissue based on the initial impedance;
- apply a first-instance electrical energy to the biological tissue, wherein a value of voltage of the first-instance electrical energy and a length of time of application of the first-instance electrical energy are both based on the first-instance size of the biological tissue;
- detect an in-process parameter during applying the first-instance electrical energy to the biological tissue, wherein the in-process parameter is (i) a value of in-process impedance of the biological tissue, (ii) a rate of change of the in-process impedance of the biological tissue, (iii) a value of in-process integrated power delivered to the biological tissue, or (iv) a combination thereof;
- determine a second-instance size of the biological tissue based on the detected in-process parameter; and
- apply a second-instance electrical energy to the biological tissue, wherein a value of voltage of the second-instance electrical energy and a length of time of application of the second-instance electrical energy are both based on the second-instance size of the biological tissue.

14. The controller according to claim 13, wherein the controller is configured to apply the second-instance electrical energy is to the biological tissue until sealing of the tissue is complete.

15. The controller according to claim 13, wherein, when the second-instance size of the biological tissue is different than the first-instance size of the biological tissue, the second-instance electrical energy to the biological tissue is different than the first-instance electrical energy to the biological tissue.

16. The controller according to claim 13, wherein, when the second-instance size of the biological tissue is the same as the first-instance size of the biological tissue, the second-instance electrical energy to the biological tissue is the same as the first-instance electrical energy to the biological tissue.

17. The controller according to claim 13, wherein the in-process parameter is the value of in-process impedance of the biological tissue.

18. The controller according to claim 17, wherein, when the first-instance size of the biological tissue based on the initial impedance is large and the value of in-process impedance of the biological tissue is greater than 200Ω, then the second-instance size of the biological tissue is determined as small, and
- wherein the second-instance electrical energy to the biological tissue is different than the first-instance electrical energy to the biological tissue.

19. The controller according to claim 13, wherein the in-process parameter is the rate of change of the in-process impedance of the biological tissue.

20. The controller according to claim 13, wherein the in-process parameter is the value of in-process integrated power delivered to the biological tissue.

* * * * *